(12) United States Patent
Borns

(10) Patent No.: US 7,939,645 B2
(45) Date of Patent: May 10, 2011

(54) REACTION BUFFER COMPOSITION FOR NUCLEIC ACID REPLICATION WITH PACKED DNA POLYMERASES

(75) Inventor: Michael Borns, Escondido, CA (US)

(73) Assignee: Agilent Technologies, Inc, Santa Clara, CA (US)

( * ) Notice: Subject to any disclaimer, the term of this patent is extended or adjusted under 35 U.S.C. 154(b) by 819 days.

(21) Appl. No.: 11/651,169

(22) Filed: Jan. 8, 2007

(65) Prior Publication Data

US 2008/0038782 A1 Feb. 14, 2008

Related U.S. Application Data

(60) Provisional application No. 60/757,120, filed on Jan. 6, 2006.

(51) Int. Cl.
*C07H 21/04* (2006.01)
*C12Q 1/68* (2006.01)
*C12P 19/34* (2006.01)

(52) U.S. Cl. ............................ 536/22.1; 435/6; 435/91.2
(58) Field of Classification Search ................. 536/22.1, 536/23.1; 530/350; 435/6, 91.2
See application file for complete search history.

(56) References Cited

U.S. PATENT DOCUMENTS

| 6,300,073 B1 * | 10/2001 | Zhao et al. .......................... 435/6 |
| 6,403,341 B1 * | 6/2002 | Barnes et al. ................. 435/91.2 |
| 6,495,350 B1 * | 12/2002 | Lee et al. ...................... 435/91.2 |
| 2008/0020396 A1 * | 1/2008 | Savoye et al. ....................... 435/6 |

FOREIGN PATENT DOCUMENTS

WO  WO 2004087868 A2 * 10/2004

* cited by examiner

*Primary Examiner* — Suryaprabha Chunduru

(57) ABSTRACT

The invention relates to compositions, methods, and kits for nucleic acid replication, including polymerase chain reaction (PCR) and mutagenesis reactions. A buffer composition is provided which allows higher concentrations of DNA polymerase to be used, resulting in greater yield of amplified product and faster reaction kinetics.

50 Claims, 1 Drawing Sheet

US 7,939,645 B2

REACTION BUFFER COMPOSITION FOR NUCLEIC ACID REPLICATION WITH PACKED DNA POLYMERASES

This application claims priority to U.S. Provisional Application Ser. No. 60/757,120, filed Jan. 6, 2006, the contents of which are incorporated herein in their entirety.

TECHNICAL FIELD

The invention relates to compositions and methods for the replication, amplification, or mutagenesis of nucleic acid sequences.

BACKGROUND

The sensitivity and kinetics of amplification techniques such as the polymerase chain reaction (PCR) are limited due to the fact that, using conventional buffers, increasing the concentration of DNA polymerase fails to accelerate the reaction or to increase the yield of amplified product. In situations where sample material is limited, or the target sequence is present in low copy number, this limitation is a significant problem. Especially in diagnostic PCR applications, where amplification is carried out in the presence of background nucleic acids and the target may be present low levels, even down to a single copy, it would be advantageous to use conditions that permit a faster rate of nucleic acid replication with greater product yield.

SUMMARY OF THE INVENTION

The invention is related to novel compositions and methods for nucleic acid replication, amplification, and mutagenesis.

The invention provides compositions useful for nucleic acid replication. The compositions comprise a mineral salt, such as potassium sulfate, and ammonium sulfate and have a mineral salt:ammonium sulfate molar ratio of 5:1 to 240:1. In some embodiments, the mineral salt concentration ranges from 50 mM to 120 mM, and the ammonium sulfate concentration ranges from 1 to 5 mM. The total cation concentration in the mineral salt component of the buffer mix is preferred to be in the range of about 50 and 120 mM. Certain embodiments of the composition also comprise magnesium sulfate, Tris sulfate, and Triton X-100. In some embodiments, the composition is essentially free of chloride and citrate anions. In some embodiments, essentially all of the anions in the composition are sulfate ions. Some embodiments of the composition include either one or more nucleotides, one or more nucleic acid polymerases, a nucleic acid template, or a primer.

Another aspect of the invention is a buffer concentrate for preparing a DNA polymerase reaction solution. Dilution of the buffer concentrate by a factor ranging from 2-fold to 20-fold yields a solution comprising mineral salt (e.g., potassium sulfate) and ammonium sulfate and having a mineral salt:ammonium sulfate molar ratio of 5:1 to 240:1. Some embodiments of the buffer concentrate include either one or more nucleotides, one or more nucleic acid polymerases, a nucleic acid template, or a primer.

In an additional aspect of the invention, a composition for nucleic acid replication or a buffer concentrate for preparing a DNA polymerase reaction solution is part of a kit. The kit provides the composition or buffer concentrate and packaging, optionally with additional reagents such as one or more DNA polymerases, nucleoside triphosphates, a primer, or a nucleic acid template.

The invention also provides a method for carrying out nucleic acid replication reactions, including PCR. The method comprises performing a DNA polymerase reaction using a composition comprising mineral salt and ammonium sulfate and having a mineral salt:ammonium sulfate molar ratio of 5:1 to 240:1.

DETAILED DESCRIPTION OF THE INVENTION

Figure 1:
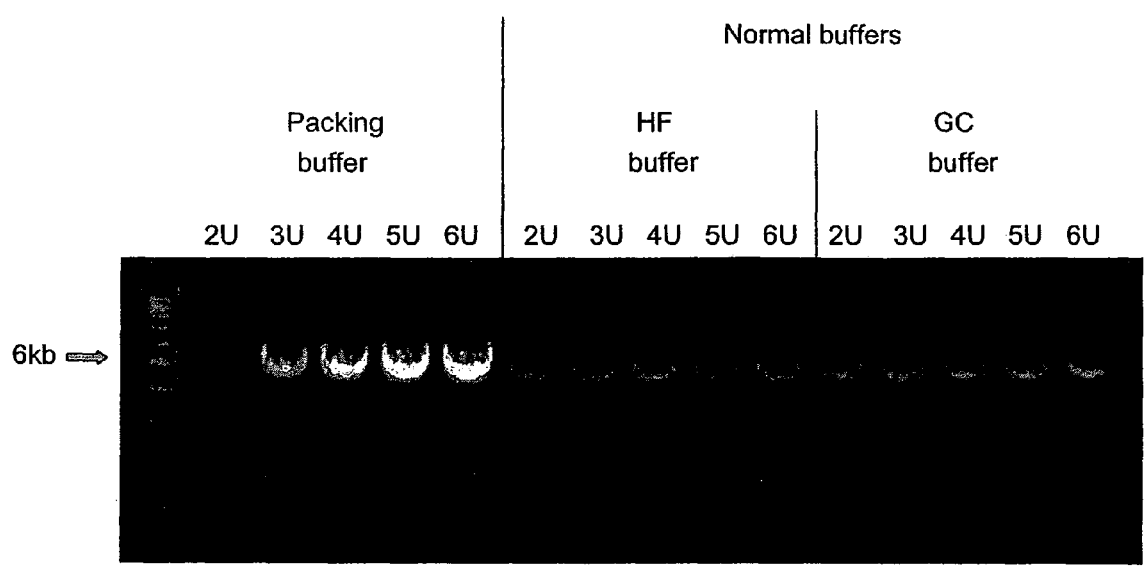
FIG. 1 shows the effect of different buffers on the concentration dependence of DNA polymerase concentration in a PCR experiment. Gel electrophoresis with ethidium bromide staining demonstrates the yield of amplified product under each condition. Only with a buffer of the present invention does the amount of product increase with elevation of the DNA polymerase concentration. See Example 1 for details.

The invention provides novel compositions and methods for performing replication of a nucleic acid. Compositions having a certain range of chemical composition enable much higher concentrations of DNA polymerase to be used, without inhibition, and resulting in far greater product yield. The compositions of the invention can also be used to decrease reaction times in a DNA polymerase reaction, including PCR.

General Definitions

As used herein, the term "mineral salt" refers to the salt of a naturally-occurring, homogeneous solid with a definite, but generally not fixed, chemical composition and an ordered atomic arrangement. Minerals that can be used as salts according to the invention, are those that are classified as metals on the periodic table of elements, and a mineral salt can, therefore, also be referred to according to the invention, as a metal salt (e.g., the salt form of a metal element). Examples of minerals include, but are not limited to potassium, cesium, magnesium, calcium, sodium, and other minerals known to those of skill in the art and that are generally classified as metals on the periodic table of elements. A "salt" refers to an ionic compound composed of cations and anions so that the product is neutral. Mineral salts useful in the instant invention include, but are not limited to, potassium sulfate, potassium chloride, potassium nitrate, magnesium chloride, cesium chloride, and cesium nitrate.

As used herein, a "polynucleotide" refers to a covalently linked sequence of nucleotides (i.e., ribonucleotides for RNA and deoxyribonucleotides for DNA) in which the 3' position of the pentose of one nucleotide is joined by a phosphodiester group to the 5' position of the pentose of the next. The term "polynucleotide" includes, without limitation, single- and double-stranded polynucleotide. The term "polynucleotide" as it is employed herein embraces chemically, enzymatically or metabolically modified forms of polynucleotide. "Polynucleotide" also embraces a short polynucleotide, often referred to as an oligonucleotide (e.g., a primer or a probe). A polynucleotide has a "5'-terminus" and a "3'-terminus" because polynucleotide phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus. As used herein, a polynucleotide sequence, even if internal to a larger polynucleotide (e.g., a sequence region within a polynucleotide), also can be said to have 5'- and 3'- ends.

As used herein, the term "oligonucleotide" refers to a short polynucleotide, typically less than or equal to 150 nucleotides long (e.g., in the range of 5 and 150, preferably in the range of 10 to 100, more preferably in the range of 15 to 50 nucleotides in length). However, as used herein, the term is also intended to encompass longer or shorter polynucleotide chains. An "oligonucleotide" may hybridize to other polynucleotides, therefore serving as a probe for polynucleotide detection, or a primer for polynucleotide chain extension.

As used herein, the term "complementary" refers to the concept of sequence complementarity between regions of two polynucleotide strands or between two regions of the same polynucleotide strand. It is known that an adenine base of a first polynucleotide region is capable of forming specific hydrogen bonds ("base pairing") with a base of a second polynucleotide region which is antiparallel to the first region if the base is thymine or uracil. Similarly, it is known that a cytosine base of a first polynucleotide strand is capable of base pairing with a base of a second polynucleotide strand which is antiparallel to the first strand if the base is guanine. A first region of a polynucleotide is complementary to a second region of the same or a different polynucleotide if, when the two regions are arranged in an antiparallel fashion, at least one nucleotide of the first region is capable of base pairing with a base of the second region. Therefore, it is not required for two complementary polynucleotides to base pair at every nucleotide position. "Complementary" refers to a first polynucleotide that is 100% or "fully" complementary to a second polynucleotide and thus forms a base pair at every nucleotide position. "Complementary" also refers to a first polynucleotide that is not 100% complementary (e.g., 90%, or 80% or 70% complementary) contains mismatched nucleotides at one or more nucleotide positions. In one embodiment, two complementary polynucleotides are capable of hybridizing to each other under high stringency hybridization conditions. For example, for membrane hybridization (e.g., Northern hybridization), high stringency hybridization conditions are defined as incubation with a radiolabeled probe in 5×SSC, 5×Denhardt's solution, 1% SDS at 65° C. Stringent washes for membrane hybridization are performed as follows: the membrane is washed at room temperature in 2×SSC/0.1% SDS and at 65° C. in 0.2×SSC/0.1% SDS, 10 minutes per wash, and exposed to film.

As used herein, the term "hybridization" or "binding" is used in reference to the pairing of complementary (including partially complementary) polynucleotide strands. Hybridization and the strength of hybridization (i.e., the strength of the association between polynucleotide strands) is impacted by many factors well known in the art including the degree of complementarity between the polynucleotides, stringency of the conditions involved affected by such conditions as the concentration of salts, the melting temperature (Tm) of the formed hybrid, the presence of other components (e.g., the presence or absence of polyethylene glycol), the molarity of the hybridizing strands and the G:C content of the polynucleotide strands.

As used herein, when one polynucleotide is said to "hybridize" to another polynucleotide, it means that there is some complementarity between the two polynucleotides or that the two polynucleotides form a hybrid under high stringency conditions. When one polynucleotide is said to not hybridize to another polynucleotide, it means that there is no sequence complementarity between the two polynucleotides or that no hybrid forms between the two polynucleotides at a high stringency condition.

As used herein, the term "template" refers to that strand of a nucleic acid molecule from which a complementary nucleic acid strand is synthesized by a nucleic acid polymerase. As used herein, the term "template dependent manner" is intended to refer to a process that involves the template dependent extension of a primer molecule (e.g., DNA synthesis by DNA polymerase). The term "template dependent manner" refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

As used herein, "synthesis" refers to an in vitro method for making a new strand of polynucleotide or elongating existing polynucleotide (i.e., DNA or RNA) in a template dependent manner. Synthesis, according to the invention, includes amplification, which increases the number of copies of a polynucleotide template sequence with the use of a polymerase. Polynucleotide synthesis (e.g., amplification) results in the incorporation of nucleotides into a polynucleotide (i.e., a primer), thereby forming a new polynucleotide molecule complementary to the polynucleotide template. The formed polynucleotide molecule and its template can be used as templates to synthesize additional polynucleotide molecules.

As used herein, "nucleic acid polymerase" refers to an enzyme that catalyzes the polymerization of nucleotides. Generally, the enzyme will initiate synthesis at the 3'-end of the primer annealed to a nucleic acid template sequence, and will proceed toward the 5' end of the template strand. "DNA polymerase" catalyzes the polymerization of deoxynucleotides. Known DNA polymerases include, for example, *Pyrococcus furiosus* (Pfu) DNA polymerase (Lundberg et al., 1991, Gene, 108: 1), *E. coli* DNA polymerase I (Lecomte and Doubleday, 1983, Nucleic Acids Res. 11:7505), T7 DNA polymerase (Nordstrom et al., 1981, J. Biol. Chem. 256: 3112), *Thermus thermophilus* (Tth) DNA polymerase (Myers and Gelfand 1991, Biochemistry 30:7661), *Bacillus stearothermophilus* DNA polymerase (Stenesh and McGowan, 1977, Biochim Biophys Acta 475:32), *Thermococcus litoralis* (Tli) DNA polymerase (also referred to as Vent DNA polymerase, Cariello et al., 1991, Nucleic Acids Res, 19: 4193), 9° Nm DNA polymerase (discontinued product from New England Biolabs), *Thermotoga maritima* (Tma) DNA polymerase (Diaz and Sabino, 1998 Braz J. Med. Res, 31:1239), *Thermus aquaticus* (Taq) DNA polymerase (Chien et al., 1976, J. Bacteoriol, 127: 1550), *Pyrococcus kodakaraensis* KOD DNA polymerase (Takagi et al., 1997, Appl. Environ. Microbiol. 63:4504), JDF-3 DNA polymerase (Patent application WO 0132887), and *Pyrococcus* GB-D (PGB-D) DNA polymerase (Juncosa-Ginesta et al., 1994, Biotechniques, 16:820). A polymerase according to the invention can be a chimeric polymerase or a mutant polymerase. An example of a chimeric polymerase according to the invention is the chimera between Pfu and DeepVent polymerases described in published US patent application 2004/0214194, which is hereby incorporated by reference in its entirety. Additional examples of chimeric DNA polymerases can include combinations of chimeric polymerases and fusion polymerases (fusions are described further below). For example a chimera between Pfu and Deep Vent can also include a fusion of one or both polymerases to the sequence non-specific DNA binding protein Sso7d or Sac7d from *Sulfolobus sulfataricus*. Such fusions are described in WO 01/92501, incorporated herein by reference.

The polymerase activity of any of the above enzymes can be determined by means known in the art. For example, the nucleotide incorporation assay of Hogrefe et al. (Methods in Enzymol. Vol. 334, pp. 91-116 (2001)) can be used. Briefly, polymerase activity can be measured as the rate of incorporation of $^{32}$P-dCTP into activated salmon sperm DNA (purchased from Pharmacia; for activation protocol see C. C. Richardson, Procedures in Nucl. Acid Res. (Cantoni and Davies, eds.), p. 263-276 (1966) at p. 264). The reaction buffer can be, for example, 50 mM Tris-HCl (pH 8.0), 5 mM $MgCl_2$, 1 mM dithiothreitol (DTT), 50 µg/ml bovine serum albumin (BSA), and 4% (v/v) glycerol. Nucleotide substrates and DNA are used in large excess, typically at least 10 times the Km for the polymerase being assayed, e.g., 200 µM each of dATP, dTTP, and dGTP, 195 µM of dCTP plus 5 µM of labeled dCTP, and 250 µg/ml of activated DNA. The reactions are quenched on ice, and aliquots of the reaction mixture are spotted onto ion exchange filters (e.g., Whatman DE81). Unincorporated nucleotide is washed through, followed by scintillation counting to measure incorporated radioactivity.

One unit of DNA polymerase activity, according to the subject invention, is defined as the amount of enzyme which catalyzes the incorporation of 10 nmoles of total dNTPs into polymeric form in 30 minutes at optimal temperature (e.g., 72° C. for Pfu DNA polymerase).

A "DNA polymerase fusion" as defined herein, is a first amino acid sequence (protein) comprising a wild type or mutant DNA polymerase, joined to a second amino acid sequence defining a polypeptide that modulates one or more activities of the DNA polymerase including, but not limited to, processivity, salt-resistance, DNA binding, strand displacement activity, polymerase activity, nucleotide binding and recognition, 3'-5' or 5'-3' exonuclease activities, proofreading, fidelity and/or decreased DNA polymerization at room temperature, wherein the first and second amino acid sequences are not found in the same relationship in nature. A "fusion" according to the invention contains two or more amino acid sequences (for example a sequence encoding a wild type or mutant DNA polymerase and a polypeptide that increases processivity and/or salt resistance) from unrelated proteins, joined to form a new functional protein. Either source sequence used in a fusion according to the invention can be a native polypeptide sequence, a portion of a native polypeptide sequence, or a mutant of all or a portion of a native polypeptide sequence. A fusion according to the invention can comprise a first amino acid sequence derived from a first polymerase species (e.g. Pfu N-terminus) and a second amino acid sequence derived from a second polymerase species (e.g. KOD C-terminus). A fusion of the invention can comprise a first amino acid sequence derived from a first polymerase and a second amino acid sequence derived from a polypeptide that is not a polymerase. The amino acid sequence derived from a polypeptide that is not a polymerase can lack enzymatic activity. DNA polymerase has been fused in frame to the helix-hairpin-helix DNA binding motifs from DNA topoisomerase V and found to have increased processivity, salt resistance and thermostability (Pavlov et al., 2002, Proc. Natl. Acad. Sci USA, 99:13510-13515). Fusion of a thioredoxin binding domain to T7 DNA polymerase enhances the processivity of the DNA polymerase fusion in the presence of thioredoxin as described in WO 97/29209, U.S. Pat. No. 5,972,603 and Bedford et al. Proc. Natl. Acad. Sci. USA 94: 479-484 (1997). Fusion of the archaeal PCNA binding domain to Taq DNA polymerase results in a DNA polymerase fusion with enhanced processivity and produces higher yields of PCR amplified DNA in the presence of PCNA (Motz, M., et al., J. Biol. Chem. 2002 May 3; 277 (18); 16179-88). Also, fusion of the sequence non-specific DNA binding protein Sso7d or Sac7d from *Sulfolobus sulfataricus* to a DNA polymerase, such as Pfu or Taq DNA polymerase, was shown to greatly increase the processivity of these DNA polymerases as disclosed in WO 01/92501 A1, which is hereby incorporated by reference in its entirety. Fusions comprising all or a portion of a DNA binding protein such as Sso7d or Sac7d are preferred for use with the invention. Especially preferred are mutants of either Sso7d or Sac7d having less than 90% sequence identity with the native Sso7d or Sac7d sequence or a portion thereof. Domain substitution of all or a portion of a DNA polymerase with the corresponding domain of a different DNA polymerase also has been described (U.S. 2002/0119461). Further details of making and using DNA polymerase fusions are found in published U.S. patent application 2005/0048530, which is hereby incorporated by reference in its entirety.

PCR enhancing factors may also be used to improve efficiency of amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.). DMSO can also be added to a polymerase reaction mixture according to the invention; DMSO can enhance polymerase activity, particularly with G-C rich templates.

As used herein, "5' to 3' exonuclease activity" or "5'→3' exonuclease activity" refers to that activity of a template-specific nucleic acid polymerase e.g. a 5'→3' exonuclease activity traditionally associated with some DNA polymerases whereby mononucleotides or oligonucleotides are removed from the 5' end of a polynucleotide in a sequential manner, (i.e., E. coli DNA polymerase I has this activity whereas the Klenow (Klenow et al., 1970, Proc. Natl. Acad. Sci., USA, 65:168) fragment does not, (Klenow et al., 1971, Eur. J. Biochem., 22:371)), or polynucleotides are removed from the 5' end by an endonucleolytic activity that may be inherently present in a 5' to 3' exonuclease activity.

FEN-1 is an approximately 40 kDa, divalent metal ion-dependent exo- and endonuclease that specifically recognizes the backbone of a 5' single-stranded flap strand and tracks down this arm to the cleavage site, which is located at the junction wherein the two strands of duplex DNA adjoin the single-stranded arm. Both the endo- and exonucleolytic activities show little sensitivity to the base at the most 5' position at the flap or nick. Both FEN-1 endo- and exonucleolytic substrate binding and cutting are stimulated by an upstream oligonucleotide (flap adjacent strand or primer). This is also the case for *E. coli* pol I. The endonuclease activity of the enzyme is independent of the 5' flap length, cleaving a 5' flap as small as one nucleotide. The endonuclease and exonuclease activities are insensitive to the chemical nature of the substrate, cleaving both DNA and RNA.

fen-b 1 genes encoding FEN-1 enzymes useful in the invention include murine fen-1, human fen-1, rat fen-1, *Xenopus laevis* fen-1, and fen-1 genes derived from four archaebacteria *Archaeglobus fulgidus, Methanococcus jannaschii, Pyrococcus furiosus* and *Pyrococcus horikoshii*. CDNA clones encoding FEN-1 enzymes have been isolated from human (GenBank Accession Nos.: NM.sub.—004111 and L37374), mouse (GenBank Accession No.: L26320), rat (GenBank Accession No.: AA819793), *Xenopus laevis* (GenBank Accession Nos.: U68141 and U64563), and *P. furiosus* (GenBank Accession No.: AF013497). The complete nucleotide sequence for *P. horikoshii* flap endonuclease has also been determined (GenBank Accession No.: AB005215). The FEN-1 family also includes the *Saccharomyces cerevisiae* RAD27 gene (GenBank Accession No.: Z28113 Y13137) and the *Saccharomyces pombe* RAD2 gene (GenBank Accession No.: X77041). The archaeal genome of *Methanobacterium thermautotrophiculum* has also been sequenced. Although the sequence similarity between FEN-1 and prokaryotic and viral 5'{character pullout}3' exonucleases is low, FEN-1s within the eukaryotic kingdom are highly conserved at the amino acid level, with the human and *S. cerevisiae* proteins being 60% identical and 78% similar. The three archaebacterial FEN-1 proteins are also, highly homologous to the eukaryotic FEN-1 enzymes (reviewed in Matsui et al., 1999., J. Biol. Chem., 274:18297, Hosfield et al., 1998b, J. Biol. Chem., 273:27154 and Lieber, 1997, BioEssays, 19:233).

A FEN nuclease according to the invention is preferably thermostable. Thermostable FEN nucleases have been isolated and characterized from a variety of thermostable organisms including four archaeabacteria. The cDNA sequence (GenBank Accession No. AF013497) and the amino acid sequence (Hosfield et al., 1998a, supra and Hosfield et al., 1998b) for *P. furiosus* flap endonuclease have been determined. The complete nucleotide sequence (GenBank Accession No.: AB005215) and the amino acid sequence (Matsui et al., supra) for *P. horikoshii* flap endonuclease have also been determined. The amino acid sequence for *M. jannaschii* (Hosfield et al., 1998b and Matsui et al., 1999 supra) and *A. fulgidus* (Hosfield et al., 1998b) flap endonuclease have also been determined.

As used herein, a "primer" refers to a type of oligonucleotide having or containing the length limits of an "oligonucleotide" as defined above, and having or containing a sequence complementary to a target polynucleotide, which hybridizes to the target polynucleotide through base pairing so to initiate an elongation (extension) reaction to incorporate a nucleotide into the oligonucleotide primer. The conditions for initiation and extension include the presence of four different deoxyribonucleoside triphosphates and a polymerization-inducing agent such as DNA polymerase or reverse transcriptase, in a suitable buffer ("buffer" includes substituents which are cofactors, or which affect pH, ionic strength, etc.) and at a suitable temperature. The primer is preferably single-stranded for maximum efficiency in amplification. "Primers" useful in the present invention are generally in the range of about 10 and 100 nucleotides in length, preferably in the range of about 17 and 50 nucleotides in length, and most preferably in the range of about 17 and 45 nucleotides in length. An "amplification primer" is a primer for amplification of a target sequence by primer extension. As no special sequences or structures are required to drive the amplification reaction, amplification primers for PCR may consist only of target binding sequences. A "primer region" is a region on a "oligonucleotide probe" or a "bridging oligonucleotide probe" which hybridizes to the target nucleic acid through base pairing so to initiate an elongation reaction to incorporate a nucleotide into the oligonucleotide primer.

"Primer extension reaction" or "synthesizing a primer extension" means a reaction between a target-primer hybrid and a nucleotide which results in the addition of the nucleotide to a 3'-end of the primer such that the incorporated nucleotide is complementary to the corresponding nucleotide of the target polynucleotide. Primer extension reagents typically include (i) a polymerase enzyme; (ii) a buffer; and (iii) one or more extendible nucleotides.

As used herein, "polymerase chain reaction" or "PCR" refers to an in vitro method for amplifying a specific polynucleotide template sequence. The PCR reaction involves a repetitive series of temperature cycles and is typically performed in a volume of 50-100 µl. The reaction mix comprises dNTPs (each of the four deoxynucleotides dATP, dCTP, dGTP, and dTTP), primers, buffers, DNA polymerase, and polynucleotide template. One PCR reaction may consist of 5 to 100 "cycles" of denaturation and synthesis of a polynucleotide molecule. The PCR process is described in U.S. Pat. Nos. 4,683,195 and 4,683,202, the disclosures of which are incorporated herein by reference.

As used herein, "target nucleic acid" refers to a nucleic acid containing an amplified region. The "amplified region," as used herein, is a region of a nucleic acid that is to be either synthesized or amplified by polymerase chain reaction (PCR). For example, an amplified region of a nucleic acid template resides between two sequences to which two PCR primers are complementary to.

As used herein, an "amplified product" refers to the double stranded polynucleotide population at the end of a PCR amplification reaction. The amplified product contains the original polynucleotide template and polynucleotide synthesized by DNA polymerase using the polynucleotide template during the PCR reaction.

The term "wild-type" refers to a gene or gene product which has the characteristics of that gene or gene product when isolated from a naturally occurring source. In contrast, the term "modified" or "mutant" refers to a gene or gene product which displays altered characteristics when compared to the wild-type gene or gene product. For example, a mutant DNA polymerase in the present invention is a DNA polymerase which exhibits a reduced uracil detection activity.

As used herein, the term "sample" refers to a biological material which is isolated from its natural environment and containing a polynucleotide. A "sample" according to the invention may consist of purified or isolated polynucleotide, or it may comprise a biological sample such as a tissue sample, a biological fluid sample, or a cell sample comprising a polynucleotide. A biological fluid includes blood, plasma, sputum, urine, cerebrospinal fluid, lavages, and leukophoresis samples. A sample of the present invention may be a plant, animal, bacterial or viral material containing a target polynucleotide. Useful samples of the present invention may be obtained from different sources, including, for example, but not limited to, from different individuals, different developmental stages of the same or different individuals, different disease individuals, normal individuals, different disease stages of the same or different individuals, individuals subjected to different disease treatment, individuals subjected to different environmental factors, individuals with predisposition to a pathology, individuals with exposure to an infectious disease (e.g., HIV). Useful samples may also be obtained from in vitro cultured tissues, cells, or other polynucleotide containing sources. The cultured samples may be taken from sources including, but are not limited to, cultures (e.g., tissue or cells) cultured in different media and conditions (e.g., pH, pressure, or temperature), cultures (e.g., tissue or cells) cultured for different period of length, cultures (e.g., tissue or cells) treated with different factors or reagents (e.g., a drug candidate, or a modulator), or cultures of different types of tissue or cells.

As used herein, a polynucleotide "isolated" from a sample is a naturally occurring polynucleotide sequence within that sample which has been removed from its normal cellular (e.g., chromosomal) environment. Thus, an "isolated" polynucleotide may be in a cell-free solution or placed in a different cellular environment.

As used herein, the term "amount" refers to an amount of a target polynucleotide in a sample, e.g., measured in µg, µmol or copy number. The abundance of a polynucleotide in the present invention is measured by the fluorescence intensity emitted by such polynucleotide, and compared with the fluorescence intensity emitted by a reference polynucleotide, i.e., a polynucleotide with a known amount.

Compositions for Nucleic Acid Replication and Their Use

A conventional reaction buffer for nucleic acid replication, such as PCR, contains a buffer such as Tris or Tricine and usually has a pH range of from 7.5 to 9.5. It further contains $Mg^{2+}$ (e.g., $MgCl_2$ or $MgSO_4$) in the range of 1-10 mM, and frequently also contains KCl at concentrations up to about 20 mM. It may further contain one or more non-ionic detergents (e.g., Trition X-100, Tween 20, or NP40) at concentrations up to 1%, and sometimes includes bovine serum albumin (BSA) in the range of from 1-100 µg/ml.

According to the invention, the yield of product can be increased and the reaction kinetics can be made faster if a new buffer formulation is used, which enables the DNA polymerase concentration in the reaction to be productively increased. The ability to use very high amounts of DNA polymerase allows dramatic increases of DNA product yield from replication reactions and/or faster reaction times than can be achieved with smaller amounts of DNA polymerase with normal reaction buffers.

According to the invention, the buffer used for a DNA polymerase reaction contains both mineral salt (e.g., potassium sulfate ($K_2SO_4$)) and ammonium sulfate ($NH_4SO_4$), in a molar ratio which is in the range of 5:1 to 240:1 of mineral salt to ammonium sulfate. The molar ratio of mineral salt to ammonium sulfate can also be, for example, from 5:1 to 80:1, from 5:1 to 50:1, from 5:1 to 45:1 or from 10:1 to 40:1. The molar ratio of mineral salt to ammonium sulfate can also be about 10:1, about 15:1, about 20:1, about 25:1, about 30:1, about 35:1, about 40:1, about 45:1, about 50:1, about 60:1, about 65:1, about 70:1, about 75:1, or about 240:1. The concentration of mineral salt can be in the range of 50 mM to 120 mM, and preferably is in the range of 80 mM to 100 mM. The ammonium sulfate concentration can be in the range of 1 mM to 5 mM. In any embodiment of the foregoing, it is preferred that the total cation concentration of the mineral salt component be in the range of 50 and 120 mM.

The buffer according to the invention can contain $Mg^{2+}$, preferably in the form of $MgSO_4$ at a concentration in the range of 1-10 mM, for example at 2 mM. The buffer can contain a pH buffering agent, such as Tris or Tricine, preferably using $SO_4^{2-}$ as the counterion, preferably at a concentration in the range of 15-50 mM, such as 30 mM, and preferably at a pH in the range of 8-11, such as pH 10 or pH 9. The buffer can also contain a detergent, such as Triton X-100 at a concentration in the range of 0.01 to 1.0%, such as 0.1%.

Examples of the buffer composition of the invention include a solution comprising 50 mM mineral salt, 1 mM ammonium sulfate, 30 mM (Tris sulfate+Tris base) adjusted to pH 10.0, 2 mM magnesium sulfate, and 0.1% Triton X-100. Another example is a solution comprising 80 mM mineral salt, 1.5 mM ammonium sulfate, 30 mM (Tris sulfate+Tris base) adjusted to pH 10.0, 2 mM magnesium sulfate, and 0.1% Triton X-100. Yet another example is a solution comprising 100 mM mineral salt, 2 mM ammonium sulfate, 30 mM (Tris sulfate+Tris base) adjusted to pH 10.0, 2 mM magnesium sulfate, and 0.1% Triton X-100.

The buffer compositions of the invention can be used with a DNA polymerase or reverse transcriptase. Preferably, they are used with DNA polymerase fusions. For example, the DNA polymerase fusion can be a Pfu-Sso7d fusion (mutants of Sso7d having less than 90% amino acid sequence identity to wild type Sso7d are preferred), for example, exo- Pfu V93R -Sso7d, which lacks 3' to 5' exonuclease activity and is uracil insensitive. See U.S. published application 2005/0048530 for further examples of DNA polymerase fusions suitable for use with the buffer compositions of the invention. The buffer compositions of the invention can also contain a polymerase enhancing factor, a Fen nuclease, or DMSO.

The buffer compositions according to the invention can be used with higher than conventional concentrations of DNA polymerase. For example, a conventional PCR reaction can use up to 1 unit of DNA polymerase fusion per 50 µl reaction, or up to 5 units of a non-fusion DNA polymerase per 50 µl reaction; higher concentrations of polymerase will not increase product yield or reaction kinetics if used with conventional buffer solutions. However, if used with a buffer composition of the present invention, the polymerase concentration can be productively increased by 2-fold to 25-fold, for example by 3-fold, 4-fold, 5-fold, 6-fold, or 8-fold, with a corresponding increase of product yield. For example, when used with the buffer compositions described herein, polymerase concentrations up to 150 units can be used. Preferably the polymerase concentration is in the range of 50 and 100 units, but can be 50 to 150 units. Reaction kinetics can also be made faster by the same range of increased polymerase concentrations. Reverse transcriptase can be used in combination with the buffer composition according to the invention in a concentration range similar to that of DNA polymerase.

The buffer compositions according to the invention can be used in DNA polymerase reaction protocols, e.g., for PCR (including RT-PCR and QPCR) or site-directed mutagenesis without making other changes to the reaction conditions. Reaction times and temperatures, thermal cycling protocols, primer sequences and concentrations, nucleotide mixtures and concentrations, hybridization probes, and dyes for such methods can generally be used with the buffer compositions of the present invention without alteration. The buffer compositions of the invention, or concentrated forms thereof, can include one or more nucleotides, nucleic acid polymerases, primers, nucleic acid templates, dyes, hybridization probes, or polymerization enhancing factors.

Sulfate ions are preferred as the anionic species in the buffer compositions of the invention. Substitution of sulfate with chloride or citrate, for example, results in some amount of inhibition relative to sulfate. In some embodiments, the buffer composition of the invention is essentially free of chloride ions and citrate ions; in other embodiments, the concentration of chloride and citrate ions is kept to a minimum, e.g., less than 5 mM, or less than 1 mM. In certain embodiments, essentially all of the anions (excluding nucleic acids, nucleotide substrates, dyes, enzymes, proteins, detergents, etc.) in the buffer composition are sulfate ions.

The buffer compositions of the invention can be prepared as concentrated stock solutions in order to accommodate the addition of other reagents, including enzymes and substrates, as is common practice in the field of nucleic acid replication reactions. The buffer composition can be prepared as concentrates with all components present at 2-fold to 20-fold higher concentrations, for example at 5-fold higher or 10-fold higher concentrations, than the desired final concentrations.

Examples of the buffer concentrates of the invention include a solution comprising 250 mM mineral salt, 5 mM ammonium sulfate, 150 mM (Tris sulfate+Tris base) adjusted to pH 10.0, 10 mM magnesium sulfate, and 0.5% Triton X-100. Another example is a solution comprising 450 mM mineral salt, 10 mM ammonium sulfate, 150 mM (Tris sulfate+Tris base) adjusted to pH 10.0, 10 mM magnesium sulfate, and 0.5% Triton X-100. Yet another example is a solution comprising 500 mM mineral salt, 10 mM ammonium sulfate, 150 mM (Tris sulfate+Tris base) adjusted to pH 10.0, 10 mM magnesium sulfate, and 0.5% Triton X-100.

The invention provides methods of performing a nucleic acid replication reaction. The methods can be applied to of nucleic acid replication reaction using a DNA polymerase, including nucleic acid amplification, PCR, RT-PCR, QPCR, random mutagenesis, and site-directed mutagenesis, in order to increase product yield or speed reaction kinetics. Such reactions are carried out using a buffer composition of the invention, for example by using a buffer concentrate of the invention to prepare the reaction solution.

The higher concentration of DNA polymerase which can be used with buffer compositions of the invention allow more rapid reaction kinetics. Therefore, the methods of the invention generally will permit the reduction of reaction times compared to previous methods. For example, when performing PCR using a buffer composition of the invention, the cycle times can be reduced because the extension phase of each cycle can be reduced.

Mineral Salts

Mineral salts useful in the present invention include a salt of a naturally occurring, inorganic, homogeneous solid with a definite, but generally not fixed, chemical composition and an ordered atomic arrangement, and generally that are produced by geological processes. Typical metal salts useful in the invention include the salts of metal elements from the periodic table. Examples of minerals or metals that can be used in salt form according to the invention include, but are not limited to, potassium, cesium, magnesium, sodium, and calcium. Preferably the mineral salt is a salt of potassium or cesium, but can includes salts of lithium, aluminum, manganese, iron, cobalt, nickel, zinc, and the like. Mineral salts can also include the bicarbonate, sulfate, chloride, carbonate, nitrate, nitrite, bromide, citrate, acetate, cyanide, oxide or phosphate salt of a metal element known to those of skill in the art. More preferably, the mineral salt is potassium chloride (KCl), potassium sulfate ($K_2SO_4$), potassium nitrate ($KNO_3$), cesium chloride (CsCl), or cesium nitrate ($CsNO_3$). In addition, a mineral salt useful in the invention can include a mixture or blend of mineral salts. Blends of mineral salts that can be used in the invention include KCl and $K_2SO_4$, KCl and $KNO_3$, KCl and CsCl, KCl and $CsNO_3$, $K_2SO_4$ and $KNO_3$, $K_2SO_4$ and CsCl, $K_2SO_4$ and $CsNO_3$, $KNO_3$ and CsCl, $KNO_3$ and $CsNO_3$, and CsCl and $CsNO_3$. The foregoing mineral salts may be used according to the invention at a concentration in the range of 50 to 120 mM, preferably in the range of 80 to 100 mM.

Regardless of the specific mineral salt species used in the reaction buffers described herein, it is preferred that the total cation concentration in the mineral salt component be in the range of about 50 and 120 mM, preferably in the range of 50 and 120 mM, and more preferably in the range of 80 and 100 mM.

Polymerases

The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT™ and DEEPVENT™ DNA polymerases, and mutants, variants and derivatives thereof (U.S. Pat. Nos. 5,436,149; 4,889,818; 4,965,188; 5,079,352; 5,614,365; 5,374,553; 5,270,179; 5,047,342; 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J. -M, et al., Nuc. Acids Res. 22(15):3259-3260 (1994)). For amplification of long nucleic acid molecules (e.g., nucleic acid molecules longer than about 3-5 Kb in length), at least two DNA polymerases are typically used, one substantially lacking 3' exonuclease activity and the other having 3' exonuclease activity. See U.S. Pat. No. 5,436,149; U.S. Pat. No. 5,512,462; Fames, W. M., Gene 112:29-35 (1992); and copending U.S. patent application Ser. No. 09/741,664, filed Dec. 21, 2000, the disclosures of which are incorporated herein in their entireties. Examples of DNA polymerases substantially lacking in 3' exonuclease activity include, but are not limited to, Taq, Tne (exo-), Tma (exo-), Pfu (exo-), Pwo (exo-) and Tth DNA polymerases, and mutants, variants and derivatives thereof. DNA polymerases useful in the invention also include a chimeric polymerase or a mutant polymerase. An example of a chimeric polymerase according to the invention is the chimera between Pfu and DeepVent polymerases described in published U.S. patent application 2004/0214194, which is hereby incorporated by reference in its entirety.

As used herein, "packed polymerase" refers to a solution containing a sufficiently high concentration of one or more nucleic acid polymerase enzymes such that loss of polymerase activity results, unless an appropriate packing buffer is used to stabilize or activate the enzymes.

As used herein, "thermostable" refers to an enzyme which is stable and active at temperatures as great as preferably in the range of about 90-100° C. and more preferably in the range of about 70-98° C. to heat as compared, for example, to a non-thermostable form of an enzyme with a similar activity. For example, a thermostable nucleic acid polymerase derived from thermophilic organisms such as *P. furiosus, M. jannaschii, A. fulgidus* or *P. horikoshii* are more stable and active at elevated temperatures as compared to a nucleic acid polymerase from *E. coli*. A representative thermostable nucleic acid polymerase isolated from *P. furiosus* (Pfu) is described in Lundberg et al., 1991, *Gene*, 108:1-6. Additional representative temperature stable polymerases include, e.g., polymerases extracted from the thermophilic bacteria *Thermus flavus, Thermus ruber, Thermus thermophilus, Bacillus stearothermophilus* (which has a somewhat lower temperature optimum than the others listed), *Thermus lacteus, Thermus rubens, Thermotoga maritima,* or from thermophilic archaea *Thermococcus litoralis,* and *Methanothermus fervidus.*

For PCR amplifications, the enzymes used in the invention are preferably thermostable. As used herein, "thermostable" refers to an enzyme which is stable to heat, is heat resistant, and functions at high temperatures, e.g., 50 to 90° C. The thermostable enzyme according to the present invention must satisfy a single criterion to be effective for the amplification reaction, i.e., the enzyme must not become irreversibly denatured (inactivated) when subjected to the elevated temperatures for the time necessary to effect denaturation of double-stranded polynucleotides. By "irreversible denaturation" as used in this connection, is meant a process bringing a permanent and complete loss of enzymatic activity. The heating conditions necessary for denaturation will depend, e.g., on the buffer salt concentration and the length and nucleotide composition of the polynucleotides being denatured, but typically range from 85° C., for shorter polynucleotides, to 105° C. for a time depending mainly on the temperature and the polynucleotide length, typically from 0.25 minutes for shorter polynucleotides, to 4.0 minutes for longer pieces of DNA. Higher temperatures may be tolerated as the buffer salt concentration and/or GC composition of the polynucleotide is increased. Preferably, the enzyme will not become irreversibly denatured at 90 to 100° C. An enzyme that does not become irreversibly denatured, according to the invention, retains at least 10%, or at least 25%, or at least 50% or more function or activity during the amplification reaction.

As used herein, "archaeal" DNA polymerase refers to a DNA polymerase that belong to either the Family B/pol I-type group (e.g., Pfu, KOD, Pfx, Vent, Deep Vent, Tgo, Pwo) or the pol II group (e.g., *Pyrococcus furiosus* DP1/DP2 2-subunit DNA polymerase). "Archaeal" DNA polymerase refers to a thermostable DNA polymerases useful in PCR and includes, but is not limited to, DNA polymerases isolated from *Pyrococcus* species *(furiosus,* species GB-D, *woesii, abysii, horikoshii), Thermococcus* species *(kodakaraensis* KOD 1, *litoralis,* species 9 degrees North-7, species JDF-3, *gorgonarius), Pyrodictium occultum,* and *Archaeoglobus fulgidus.* It is estimated that suitable archaea exhibit maximal growth temperatures of >80-85° C. or optimal growth temperatures of >70-80° C. Appropriate PCR enzymes from the archaeal pol I DNA polymerase group are commercially available, including Pfu (Stratagene), KOD (Toyobo), Pfx (Life Technologies, Inc.), Vent (New England BioLabs), Deep Vent (New England BioLabs), Tgo (Roche), and Pwo (Roche). Additional archaea related to those listed above are described in Archaea: A Laboratory Manual (Robb, F. T. and Place, A. R., eds.), Cold Spring Harbor Laboratory Press, Cold Spring Harbor, N.Y., 1995.

As used herein, useful "Taq" DNA polymerase includes wild type Taq DNA polymerase and mutant forms of Taq DNA polymerase with reduced fidelity (e.g., Patel et al., 2001, J. Biol. Chem. 276: 5044, hereby incorporated by reference).

Some naturally occurring thermostable DNA polymerases possess enzymatically active 3' to 5' exonuclease domains, providing a natural proofreading capability and, thus, exhibiting higher fidelity than Taq DNA polymerase. However, these DNA polymerases also show slower DNA extension rates and an overall lower processivity when compared to Taq DNA polymerase.

Multiple enzyme assemblages can also be used in PCR, for example, combining Taq polymerase and a proofreading enzyme, such as Pfu polymerase or Vent DNA polymerase. Such multiple-enzyme mixtures exhibit higher PCR efficiency and reduced error rates when compared to Taq polymerase alone (Barnes, PNAS USA 91:2216-2220 (1994)).

Useful variants of Taq polymerase have been developed through deletion/truncation techniques. The Stoffel fragment, for example, is a 544 amino acid C-terminal truncation of Taq DNA polymerase, possessing an enzymatically active 5' to 3' polymerase domain but lacking 3' to 5' exonuclease and 5' to 3' exonuclease activity. Other commercially available thermostable polymerases have been developed by mutation. Examples include Vent (exo-) and Deep Vent (exo-) (New England Biolabs, Beverly, Mass.), which are point mutations of naturally-occurring polymerases.

As used herein in reference to a DNA polymerase, the term DNA polymerase includes a "functional fragment thereof". A "functional fragment thereof" refers to a portion of a wild-type or mutant DNA polymerase that encompasses less than the entire amino acid sequence of the polymerase and which retains the ability, under at least one set of conditions, to catalyze the polymerization of a polynucleotide. Such a functional fragment may exist as a separate entity, or it may be a constituent of a larger polypeptide, such as a fusion protein.

As used herein, "proofreading" activity refers to 3' to 5' exonuclease activity of a DNA polymerase. A "non-proof-reading" enyzme refers to a DNA polymerase that is "3' to 5' exonuclease deficient" or "3' to 5' exo-". As used herein, "3' to 5' exonuclease deficient" or "3' to 5' exo-" refers to an enzyme that substantially lacks the ability to remove incorporated nucleotides from the 3' end of a DNA polymer. DNA polymerase exonuclease activities, such as the 3' to 5' exonuclease activity exemplified by members of the Family B polymerases, can be lost through mutation, yielding an exonuclease-deficient polymerase. As used herein, a DNA polymerase that is deficient in 3' to 5' exonuclease activity substantially lacks 3' to 5' exonuclease activity. "Substantially lacks" encompasses a lack of activity of, for example, 0.03%, 0.05%, 0.1%, 1%, 5%, 10%, 20%, 50%, or even complete lack of the exonuclease activity relative to the parental enzyme. Methods used to generate and characterize 3' to 5' exonuclease DNA polymerases as well as mutations that reduce or eliminate 3' to 5' exonuclease activity are disclosed in the pending U.S. patent application Ser. No. 09/698,341 (Sorge et al; filed Oct. 27, 2000). Additional mutations that reduce or eliminate 3' to 5' exonuclease activity are known in the art and contemplated herein.

There are a variety of commercially available Pol I DNA polymerases, some of which have been modified to reduce or abolish 5' to 3' exonuclease activity. Methods used to eliminate 5' to 3' exonuclease activity of pol I DNA polymerases include: mutagenesis (as described in Xu et al., 1997, *J. Mol. Biol.,* 268:284 and Kim et al., 1997, *Mol. Cells,* 7:468); N-truncation by proteolytic digestion (as described in Klenow et al., 1971, *Eur. J. Biochem.,* 22: 371); or N-truncation by cloning and expressing as C-terminal fragments (as described in Lawyer et al., 1993, *PCR Methods Appl.,* 2:275).

The invention also contemplates DNA polymerases in combination with accessory factors, for example as described in U.S. Pat. No. 6,333,158, and WO 01/09347 A2, hereby incorporated by reference in its entirety.

Polymerase Chain Reaction

The technique of PCR is described in numerous publications, including, PCR: A Practical Approach, M. J. McPherson, et al., IRL Press (1991), PCR Protocols: A Guide to Methods and Applications, by Innis, et al., Academic Press (1990), and PCR Technology: Principals and Applications for DNA Amplification, H. A. Erlich, Stockton Press (1989). PCR is also described in many U.S. patents, including U.S.

Pat. Nos. 4,683,195; 4,683,202; 4,800,159; 4,965,188; 4,889,818; 5,075,216; 5,079,352; 5,104,792; 5,023,171; 5,091,310; and 5,066,584, each of which is herein incorporated by reference.

Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR; Mullis and Faloona, 1987, Methods Enzymol., 155:335). One PCR reaction may consist of 5 to 100 "cycles" of denaturation and synthesis of a nucleic acid molecule. PCR amplifications with an exo- DNA polymerase inherently will result in generating mutated amplified product.

The PCR reaction involves a repetitive series of temperature cycles and is typically performed in a volume of 10-100 μl. The reaction mix comprises dNTPs (each of the four deoxynucleotides dATP, dCTP, dGTP, and dTTP), primers, buffers, DNA polymerase, and nucleic acid template. The PCR reaction comprises providing a set of oligonucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of oligonucleotide primers" or "a set of PCR primers" can comprise two, three, four or more primers.

A PCR primer can be a single stranded DNA or RNA molecule that can hybridize to a nucleic acid template and prime enzymatic synthesis of a second nucleic acid strand. A PCR primer useful according to the invention is in the range of 10 to 100 nucleotides in length, preferably 17-50 nucleotides in length and more preferably 17-45 nucleotides in length.

Probes and primers are typically prepared by biological or chemical synthesis, although they can also be prepared by biological purification or degradation, e.g., endonuclease digestion.

For short sequences such as probes and primers used in the present invention, chemical synthesis is frequently more economical as compared to biological synthesis. For longer sequences standard replication methods employed in molecular biology can be used such as the use of M13 for single stranded DNA as described by Messing, 1983, Methods Enzymol. 101:20-78. Chemical methods of polynucleotide or oligonucleotide synthesis include phosphotriester and phosphodiester methods (Narang, et al., Meth. Enzymol. (1979) 68:90) and synthesis on a support (Beaucage, et al., Tetrahedron Letters. (1981) 22:1859-1862) as well as phosphoramidate technique, Caruthers, M. H., et al., Methods in Enzymology (1988)154:287-314 (1988), and others described in "Synthesis and Applications of DNA and RNA," S. A. Narang, editor, Academic Press, New York, 1987, and the references contained therein.

Use of a labeled probe generally in conjunction with the amplification of a target polynucleotide, for example, by PCR, e.g., is described in many references, such as Innis et al., editors, PCR Protocols (Academic Press, New York, 1989); Sambrook et al., Molecular Cloning, Second Edition (Cold Spring Harbor Laboratory, New York, 1989), all of which are hereby incorporated herein by reference. In some embodiments, the binding site of the probe is located between the PCR primers used to amplify the target polynucleotide. In other embodiments, the oligonucleotide probe complex acts as a primer. In another embodiment, the oligonucleotide probe complex binds to a target nucleic acid present in a primer incorporated into the amplicon. Preferably, PCR is carried out using Taq DNA polymerase, e.g., Amplitaq (Perkin-Elmer, Norwalk, Conn.), or an equivalent thermostable DNA polymerase, and the annealing temperature of the PCR is about 5° C. to 10° C. below the melting temperature of the oligonucleotide probes employed.

As used herein, the term "repeating one or more additional subsequent PCR amplification reactions" refers to the subsequent performance of one or more additional PCR amplification reactions comprising incubating a nucleic acid template, at least two PCR primers, an error-prone DNA polymerase under conditions which permit amplification of the nucleic acid template. A subsequent PCR reaction comprises said incubating step using the PCR amplified product of a preceding PCR amplification as template. The amplified product of a preceding PCR amplification reaction may be purified before being used as template for a subsequent PCR reaction by means known in the art, e.g., phenol extraction/ethanol precipitation or column purification. The template for a subsequent PCR amplification reaction may be a portion of or the total amplified product of a preceding PCR amplification. For each subsequent PCR amplification, fresh reagents (e.g., reaction buffer, dNTP, DNA polymerase, primers) are added to the reaction mixture. If a portion of the amplified product of a preceding PCR amplification is used, the volume of a subsequent PCR reaction may be the same as the preceding PCR reaction. If the total amplified product of a preceding PCR reaction is used as template, a subsequent PCR reaction will have larger volume than the preceding PCR reaction.

The PCR reaction involves a repetitive series of temperature cycles and is typically performed in a volume of 10-100 μl. The reaction mix comprises dNTPs (each of the four deoxynucleotides dATP, dCTP, dGTP, and dTTP), primers, buffers, DNA polymerase, and polynucleotide template. PCR requires two primers that hybridize with the double-stranded target polynucleotide sequence to be amplified. In PCR, this double-stranded target sequence is denatured and one primer is annealed to each strand of the denatured target. The primers anneal to the target polynucleotide at sites removed from one another and in orientations such that the extension product of one primer, when separated from its complement, can hybridize to the other primer. Once a given primer hybridizes to the target sequence, the primer is extended by the action of a DNA polymerase. The extension product is then denatured from the target sequence, and the process is repeated.

In successive cycles of this process, the extension products produced in earlier cycles serve as templates for DNA synthesis. Beginning in the second cycle, the product of amplification begins to accumulate at a logarithmic rate. The amplification product is a discrete double-stranded DNA molecule comprising: a first strand which contains the sequence of the first primer, eventually followed by the sequence complementary to the second primer, and a second strand which is complementary to the first strand.

Due to the enormous amplification possible with the PCR process, small levels of DNA carryover from samples with high DNA levels, positive control templates or from previous amplifications can result in PCR product, even in the absence of purposefully added template DNA. If possible, all reaction mixes are set up in an area separate from PCR product analysis and sample preparation. The use of dedicated or disposable vessels, solutions, and pipettes (preferably positive displacement pipettes) for RNA/DNA preparation, reaction mixing, and sample analysis will minimize cross contamination. See also Higuchi and Kwok, 1989, Nature, 339:237-238 and Kwok, and Orrego, in: Innis et al. eds., 1990, *PCR Protocols: A Guide to Methods and Applications*, Academic Press, Inc., San Diego, Calif., which are incorporated herein by reference.

PCR enhancing factors may also be used to improve efficiency of the amplification. As used herein, a "PCR enhancing factor" or a "Polymerase Enhancing Factor" (PEF) refers to a complex or protein possessing polynucleotide polymerase enhancing activity (Hogrefe et al., 1997, Strategies 10:93-96; and U.S. Pat. No. 6,183,997, both of which are hereby incorporated by references). For Pfu DNA polymerase, PEF comprises either P45 in native form (as a complex of P50 and P45) or as a recombinant protein. In the native complex of Pfu P50 and P45, only P45 exhibits PCR enhancing activity. The P50 protein is similar in structure to a bacterial flavoprotein. The P45 protein is similar in structure to dCTP deaminase and dUTPase, but it functions only as a dUTPase converting dUTP to dUMP and pyrophosphate. PEF, according to the present invention, can also be selected from the group consisting of: an isolated or purified naturally occurring polymerase enhancing protein obtained from an archeabacteria source (e.g., *Pyrococcus furiosus*); a wholly or partially synthetic protein having the same amino acid sequence as Pfu P45, or analogs thereof possessing polymerase enhancing activity; polymerase-enhancing mixtures of one or more of said naturally occurring or wholly or partially synthetic proteins; polymerase-enhancing protein complexes of one or more of said naturally occurring or wholly or partially synthetic proteins; or polymerase-enhancing partially purified cell extracts containing one or more of said naturally occurring proteins (U.S. Pat. No. 6,183,997, supra). The PCR enhancing activity of PEF is defined by means well known in the art. The unit definition for PEF is based on the dUTPase activity of PEF (P45), which is determined by monitoring the production of pyrophosphate (PPi) from dUTP. For example, PEF is incubated with dUTP (10 mM dUTP in 1× cloned Pfu PCR buffer) during which time PEF hydrolyzes dUTP to dUMP and PPi. The amount of PPi formed is quantitated using a coupled enzymatic assay system that is commercially available from Sigma (#P7275). One unit of activity is functionally defined as 4.0 nmole of PPi formed per hour (at 85° C.).

Other PCR additives may also affect the accuracy and specificity of PCR reactions. EDTA less than 0.5 mM may be present in the amplification reaction mix. Detergents such as Tween-20™ and Nonidet™ P-40 are present in the enzyme dilution buffers. A final concentration of non-ionic detergent approximately 0.1% or less is appropriate, however, 0.01-0.05% is preferred and will not interfere with polymerase activity. Similarly, glycerol is often present in enzyme preparations and is generally diluted to a concentration of 1-20% in the reaction mix. Glycerol (5-10%), formamide (1-5%) or DMSO (2-10%) can be added in PCR for template DNA with high GC content or long length (e.g., >1 kb). These additives change the Tm (melting temperature) of primer-template hybridization reaction and the thermostability of polymerase enzyme. BSA (up to 0.8 μg/μl) can improve efficiency of PCR reaction. Betaine (0.5-2M) is also useful for PCR over high GC content and long fragments of DNA. Tetramethylammonium chloride (TMAC, >50 mM), Tetraethylammonium chloride (TEAC), and Trimethylamine N-oxide (TMANO) may also be used. Test PCR reactions may be performed to determine optimum concentration of each additive mentioned above.

The invention provides for additives including, but not limited to antibodies (for hot start PCR) and ssb (single strand DNA binding protein; higher specificity). The invention also contemplates mutant archael DNA polymerases in combination with accessory factors, for example as described in U.S. Pat. No. 6,333,158, and WO 01/09347 A2, hereby incorporated by reference in its entirety.

Various specific PCR amplification applications are available in the art (for reviews, see for example, Erlich, 1999, *Rev Immunogenet.*, 1:127-34; Prediger 2001, *Methods Mol. Biol.* 160:49-63; Jurecic et al., 2000, *Curr. Opin. Microbiol.* 3:316-21; Triglia, 2000, *Methods Mol. Biol.* 130:79-83; MaClelland et al., 1994, *PCR Methods Appl.* 4:S66-81; Abramson and Myers, 1993, *Current Opinion in Biotechnology* 4:41-47; each of which is incorporated herein by reference).

The subject invention can be used in PCR applications including, but not limited to: (i) Hot-start PCR which reduces non-specific amplification. (ii) Nested PCR which synthesizes more reliable product using an outer set of primers and an inner set of primers. (iii) Inverse PCR for amplification of regions flanking a known sequence. In this method, DNA is digested, the desired fragment is circularized by ligation, then PCR using primer complementary to the known sequence extending outwards. (iv) AP-PCR (arbitrarily primed)/RAPD (randomly amplified polymorphic DNA). These methods create genomic fingerprints from species with little-known target sequences by amplifying using arbitrary oligonucleotides. (v) RT-PCR which uses RNA-directed DNA polymerase (e.g., reverse transcriptase) to synthesize cDNAs which is then used for PCR. This method is extremely sensitive for detecting the expression of a specific sequence in a tissue or cell. It may also be used to quantify mRNA transcripts. (vi) RACE (rapid amplification of cDNA ends). This is used where information about DNA/protein sequence is limited. The method amplifies 3' or 5' ends of cDNAs generating fragments of cDNA with only one specific primer each (plus one adaptor primer). Overlapping RACE products can then be combined to produce full length cDNA. (vii) DD-PCR (differential display PCR) which is used to identify differentially expressed genes in different tissues. The first step in DD-PCR involves RT-PCR, then amplification is performed using short, intentionally nonspecific primers. (viii) Multiplex-PCR in which two or more unique targets of DNA sequences in the same specimen are amplified simultaneously. One DNA sequence can be used as a control to verify the quality of PCR. (ix) Q/C-PCR (Quantitative comparative) which uses an internal control DNA sequence (but of a different size) which competes with the target DNA (competitive PCR) for the same set of primers. (x) Recusive PCR which is used to synthesize genes. Oligonucleotides used in this method are complementary to stretches of a gene (>80 bases), alternately to the sense and to the antisense strands with ends overlapping (~20 bases). (xi) Asymmetric PCR. (xii) In Situ PCR. (xiii) Site-directed PCR Mutagenesis.

This invention is not limited to any particular amplification system. As other systems are developed, those systems may benefit by practice of this invention.

Temperature stable polymerases are preferred in a thermocycling process wherein double stranded nucleic acids are denatured by exposure to a high temperature (about 95° C.) during the PCR cycle.

One of average skill in the art may also employ other PCR parameters to increase the fidelity of the synthesis/amplification reaction. It has been reported that PCR fidelity may be affected by factors such as changes in dNTP concentration, units of enzyme used per reaction, pH, and the ratio of $Mg^{2+}$ to dNTPs present in the reaction (Mattila et al., 1991, supra).

$Mg^{2+}$ concentration affects the annealing of the oligonucleotide primers to the template DNA by stabilizing the primer-template interaction, it also stabilizes the replication complex of polymerase with template-primer. It can therefore also increase non-specific annealing and produce undesirable PCR products (gives multiple bands in gel). When non-specific amplification occurs, $Mg^{2+}$ may need to be lowered or EDTA can be added to chelate $Mg^{2+}$ to increase the accuracy and specificity of the amplification.

Other divalent cations such as $Mn^{2+}$, or $Co^{2+}$ can also affect DNA polymerization. Suitable cations for each DNA polymerase are known in the art (e.g., in *DNA Replication* $2^{nd}$ edition, supra). Divalent cation is supplied in the form of a salt such $MgSO_4$ or $MnSO_4$. Usable cation concentrations in a Tris buffer are for $MnSO_4$ from 0.5 to 7 mM, preferably, in the range of 0.5 and 2 mM, and for $MgSO_4$ from 0.5 to 10 mM.

Monovalent cation required by DNA polymerase may be supplied by the potassium, sodium, ammonium, or lithium, preferably with sulfate as the anion. For $KSO_4$, the concentration is in the range of 1 and 200 mM, preferably the concentration is in the range of 40 and 100 mM, although the optimum concentration may vary depending on the polymerase used in the reaction.

Deoxyribonucleoside triphosphates (dNTPs) are added as solutions of the salts of dATP, dCTP, dGTP, dUTP, and dTTP, such as disodium or lithium salts. In the present method, a final concentration in the range of 1 µM to 2 mM each is suitable, and 100-600 µM is preferable, although the optimal concentration of the nucleotides may vary in the PCR reaction depending on the total dNTP and divalent metal ion concentration, and on the buffer, salts, particular primers, and template. For longer products, i.e., greater than 1500 bp, 500 µM of each dNTP may be preferred when using a Tris buffer.

dNTPs chelate divalent cations; therefore the amount of divalent cations used may need to be changed according to the dNTP concentration in the reaction. Excessive amount of dNTPs (e.g., larger than 1.5 mM) can increase the error rate and possibly inhibit DNA polymerases. Lowering the dNTP (e.g., to 10-50 µM) may reduce the error rate. PCR reactions for amplifying larger size templates may need more dNTPs.

PCR is a very powerful tool for DNA amplification and therefore very little template DNA is needed. However, in some embodiments, to reduce the likelihood of error, a higher DNA concentration may be used. However, too many templates may increase the amount of contaminants and reduce efficiency.

Usually, up to 3 µM of primers may be used, but high primer to template ratio can result in non-specific amplification and primer-dimer formation. Therefore it is usually necessary to check primer sequences to avoid primer-dimer formation.

Denaturation time may be increased if the template GC content is high. Higher annealing temperature may be needed for primers with high GC content or longer primers. Gradient PCR is a useful way of determining the annealing temperature. Extension time should be extended for larger PCR product amplifications. However, the extension time may need to be reduced whenever possible to limit damage to the polymerase. The number of cycles can be increased if the template number is very low, and decreased if template number is high.

As used herein, "mutant" polymerase refers to a DNA polymerase comprising one or more mutations that modulate one or more activities of the DNA polymerase including, but limited to, DNA polymerization activity, base analog detection activities, reverse transcriptase activity, processivity, salt resistance, DNA binding, strand displacement activity, nucleotide binding and recognition, 3' to 5' or 5' to 3' exonuclease activities, proofreading, fidelity, or decreases DNA polymerization at room temperature. A "mutant" polymerase as defined herein, includes a polymerase comprising one or more amino acid substitutions, one or more amino acid insertions, a truncation, or an internal deletion. A "mutant" polymerase as defined herein includes non-chimeric and chimeric polymerases.

There are 3 classes of eubacterial DNA polymerases, pol I, II, and III. Enzymes in the Pol I DNA polymerase family possess 5' to 3' exonuclease activity, and certain members also exhibit 3' to 5' exonuclease activity. Pol II DNA polymerases naturally lack 5' to 3' exonuclease activity, but do exhibit 3' to 5' exonuclease activity. Pol III DNA polymerases represent the major replicative DNA polymerase of the cell and are composed of multiple subunits. The pol III catalytic subunit lacks 5' to 3' exonuclease activity, but in some cases 3' to 5' exonuclease activity is located in the same polypeptide. There are no commercial sources of eubacterial pol II and pol III DNA polymerases. There are a variety of commercially available Pol I DNA polymerases, some of which have been modified to reduce or abolish 5' to 3' exonuclease activity.

Polymerase mutagenesis has been used to develop new and useful nucleic acid polymerase variants. For example, naturally occurring DNA polymerases strongly discriminate against the incorporation of nucleotide analogues. This property contributes to the fidelity of DNA replication and repair. However, the incorporation of nucleotide analogues is useful for many DNA synthesis applications, especially DNA sequencing. Hence, a DNA polymerase that lacks associated exonucleolytic activity, either 5'-nuclease activity or 3' to 5' exonuclease activity, is preferred for DNA sequencing. In order to generate thermostable DNA polymerases with reduced nucleotide discrimination, site-directed mutagenesis studies were initiated and resulted in the identification of mutant forms of a number of thermostable DNA polymerases with the requisite activities suitable for DNA sequencing (U.S. Pat. No. 5,466,591, incorporated herein by reference).

Yet another approach to modifying the property of a DNA polymerase is to generate DNA polymerase fusions in which one or more protein domains having the requisite activity are combined with a DNA polymerase. DNA polymerase has been fused in frame to the helix-hairpin-helix DNA binding motifs from DNA topoisomerase V and shown to increase processivity, salt resistance and thermostability of the chimeric DNA polymerase as described in Pavlov et al., 2002, Proc. Natl. Acad. Sci USA, 99:13510-13515. Fusion of the thioredoxin binding domain to T7 DNA polymerase enhances the processivity of the DNA polymerase fusion in the presence of thioredoxin as described in WO 97/29209, U.S. Pat. No. 5,972,603 and Bedford et al. Proc. Natl. Acad. Sci. USA 94: 479-484 (1997). Fusion of the archaeal PCNA binding domain to Taq DNA polymerase results in a DNA polymerase fusion that in the presence of PCNA has enhanced processivity and produces higher yields of PCR amplified DNA (Motz, M., et al., J. Biol. Chem. 2002 May 3; 277 (18); 16179-88). Also, fusion of the sequence non-specific DNA binding protein Sso7d or Sac7d from *Sulfolobus sulfataricus* to a DNA polymerase, such as Pfu or Taq DNA polymerase, was shown to greatly increase the processivity of these DNA polymerases as disclosed in WO 01/92501 A1 which is hereby incorporated by reference in its entirety. DNA polymerase fusions useful in combination with the buffer compositions described herein include Pfu fused to the DNA binding protein Sso7d (or the DNA binding domain thereof; a Pfu-Sso7d fusion), an exo-Pfu-Sso7d fusion, or exo-Pfu-Sso7d fusion in which amino acid V93 of Pfu is mutated (a exo-Pfu-V93R-Sso7d fusion). Other fusions can be a combination of a fusion and a chimeric DNA polymerase. For example, a preferred chimeric/fusion includes a chimera between Pfu and *Pyrococcus* species GB-D fused to the DNA binding protein Sso7D, or the DNA binding domain thereof. Domain substitution of all or a portion of a DNA polymerase with the corresponding domain of a different DNA polymerase has also been described (U.S. 2002/0119461).

Direct comparison of DNA polymerases from diverse organisms indicates that the domain structure of these enzymes is highly conserved and in many instances, it is possible to assign a particular function to a well-defined domain of the enzyme. For example, the six most conserved C-terminal regions, spanning approximately 340 amino acids, are located in the same linear arrangement and contain highly conserved motifs that form the metal and dNTP binding sites and the cleft for holding the DNA template and are therefore essential for the polymerization function. In another example, the three amino acid regions containing the critical residues in the *E. coli* DNA polymerase I involved in metal binding, single-stranded DNA binding, and catalysis of the 3'-5' exonuclease reaction are located in the amino-terminal half and in the same linear arrangement in several prokaryotic and eukaryotic DNA polymerases. The location of these conserved regions provides a useful model to direct genetic modifications for preparing mutant DNA polymerase with modified activities while conserving desired functions e.g. template recognition.

For example, a mutant DNA polymerase can be generated by genetic modification (e.g., by modifying the DNA sequence of a wild-type DNA polymerase). A number of methods are known in the art that permit the random as well as targeted mutation of DNA sequences (see for example, Ausubel et. al. *Short Protocols in Molecular Biology* (1995) 3$^{rd}$ Ed. John Wiley & Sons, Inc.). In addition, there are a number of commercially available kits for site-directed mutagenesis, including both conventional and PCR-based methods. Examples include the EXSITE™ PCR-Based Site-directed Mutagenesis Kit available from Stratagene (Catalog No. 200502) and the QUIKCHANGE™ Site-directed mutagenesis Kit from Stratagene (Catalog No. 200518), and the CHAMELEON® double-stranded Site-directed mutagenesis kit, also from Stratagene (Catalog No. 200509).

Older methods of site-directed mutagenesis known in the art rely on sub-cloning of the sequence to be mutated into a vector, such as an M13 bacteriophage vector, that allows the isolation of single-stranded DNA template. In these methods, one anneals a mutagenic primer (i.e., a primer capable of annealing to the site to be mutated but bearing one or more mismatched nucleotides at the site to be mutated) to the single-stranded template and then polymerizes the complement of the template starting from the 3' end of the mutagenic primer. The resulting duplexes are then transformed into host bacteria and plaques are screened for the desired mutation.

More recently, site-directed mutagenesis has employed PCR methodologies, which have the advantage of not requiring a single-stranded template. In addition, methods have been developed that do not require sub-cloning. Several issues must be considered when PCR-based site-directed mutagenesis is performed. First, in these methods it is desirable to reduce the number of PCR cycles to prevent expansion of undesired mutations introduced by the polymerase. Second, a selection must be employed in order to reduce the number of non-mutated parental molecules persisting in the reaction. Third, an extended-length PCR method is preferred in order to allow the use of a single PCR primer set. And fourth, because of the non-template-dependent terminal extension activity of some thermostable polymerases it is often necessary to incorporate an end-polishing step into the procedure prior to blunt-end ligation of the PCR-generated mutant product.

Methods of random mutagenesis, which will result in a panel of mutants bearing one or more randomly situated mutations, exist in the art. Such a panel of mutants may then be screened for desired activity such as those exhibiting properties including but not limited to reduced DNA polymerization activity, 3'-5' exonuclease deficiency, or processivity relative to the wild-type polymerase (e.g., by measuring the incorporation of 10 nmoles of dNTPs into polymeric form in 30 minutes in the presence of 200 µM dUTP and at the optimal temperature for a given DNA polymerase). An example of a method for random mutagenesis is the so-called "error-prone PCR method". As the name implies, the method amplifies a given sequence under conditions in which the DNA polymerase does not support high fidelity incorporation. The conditions encouraging error-prone incorporation for different DNA polymerases vary, however one skilled in the art may determine such conditions for a given enzyme. A key variable for many DNA polymerases in the fidelity of amplification is, for example, the type and concentration of divalent metal ion in the buffer. The use of manganese ion and/or variation of the magnesium or manganese ion concentration may therefore be applied to influence the error rate of the polymerase.

Genes for desired mutant DNA polymerases generated by mutagenesis may be sequenced to identify the sites and number of mutations. For those mutants comprising more than one mutation, the effect of a given mutation may be evaluated by introduction of the identified mutation to the wild-type gene by site-directed mutagenesis in isolation from the other mutations borne by the particular mutant. Screening assays of the single mutant thus produced will then allow the determination of the effect of that mutation alone.

Typically, the 5' to 3' exonuclease activity, 3' to 5' exonuclease activity, discriminatory activity, and fidelity can be affected by substitution of amino acids typically which have different properties. For example, an acidic amino acid such as Asp may be changed to a basic, neutral or polar but uncharged amino acid such as Lys, Arg, His (basic); Ala, Val, Leu, Ile, Pro, Met, Phe, Trp (neutral); or Gly, Ser, Thr, Cys, Tyr, Asn or Gln (polar but uncharged). Glu may be changed to Asp, Ala, Val Leu, Ile, Pro, Met, Phe, Trp, Gly, Ser, Thr, Cys, Tyr, Asn or Gln.

Methods of measuring the efficiency of a DNA polymerase are described in PCR Primer: A Laboratory Manual, 1995, CSHL Press, Cha and Thilly, pp. 37-51. Methods of measuring template length amplification capability are described in Proc Natl. Acad. Sci USA, 2002, 99:596-601 and J. Biotechnol., 2001, 88:141-149. Methods of measuring specificity of a DNA polymerase are described in J. Biochem. (Tokyo), 1999, 126:762-8. Methods of measuring thermostability of a DNA polymerase are described in FEMS Microbiol. Lett, 2002, 217:89-94. Methods of measuring nucleotide binding and recognition are described in J. Mol. Biol., 2002, 322:719-729 and Nucleic Acids Res., 2002, 30:605-13.

Kits

The invention provides novel compositions and methods for nucleic acid replication reactions such as PCR and mutagenesis. The invention also contemplates a kit format which comprises a package unit having one or more containers of the subject composition and in some embodiments including containers of various reagents used for polynucleotide synthesis, including synthesis in PCR. The kit may also contain one or more of the following items: polymerization enzymes, polynucleotide precursors (e.g., nucleotides), primers, templates, probes, polymerization enhancing factors, dyes, buffers, instructions, and controls. The kits may include containers of reagents mixed together in suitable proportions for performing the methods in accordance with the invention. Reagent containers preferably contain reagents in unit quantities that obviate measuring steps when performing the subject methods. One kit according to the invention also contains a DNA yield standard for the quantitation of the PCR product yields from a stained gel.

The example below is non-limiting and is merely representative of various aspects and features of the subject invention. The contents of all patents, patent publications, and other citations referred to herein are hereby incorporated by reference in their entirety.

EXAMPLE 1

A 5× packing PCR reaction buffer was prepared according to the table below.

| Material | Source | Stock | Amount | Final 5× Concentration |
|---|---|---|---|---|
| Tris sulfate/Tris base | Sigma, ultrapure | 1 M stock solution, pH 10.0 | 75 ml | 150 mM |
| Potassium sulfate | Sigma, ultrapure | 0.5 M stock solution | 200 ml | 200 mM |
| Ammonium sulfate | J. T. Baker, ultrapure | 1 M stock solution | 2.5 ml | 5 mM |
| Magnesium sulfate | Sigma, ultrapure | 1 M stock solution | 5 ml | 10 mM |
| Triton X-100 | Sigma, ultrapure | 10% stock solution | 25 ml | 0.5% |
| Water | Ultrapure, DNase-RNase-free | | 192.5 ml | |

The Tris sulfate 1M stock solution is prepared by mixing a solution of 1M Tris base (Sigma, ultrapure) with an appropriate amount of a solution of 1M Tris sulfate (Sigma, ultrapure) to obtain a pH of 10.0.

Amplification of a 6 kb DNA standard (human beta globin) was performed using the 5× packing PCR reaction buffer to obtain a final reaction solution with 1× concentrations. Final concentration or amount of reagents per 50 μl reaction was 200 μM of each of the four deoxyribonucleoside triphosphates, 100 ng of human genomic DNA template, 0.2 μM of each primer, 2U PEF, and 2-6U of Phusion DNA polymerase (Finnzymes OY (Espoo, Finland)). Amplification was carried out as follows: 95° C. for 2 minutes for 1 cycle; 95° C. for 20 seconds, 58° C. for 20 seconds, 72° C. for 1 minute 30 seconds for 30 cycles; 72° C. for 3 minutes for 1 cycle. Thermocycling was performed on either an MJ research PTC-200 DNA Engine or an Applied Biosystems Gene Amp PCR System 9600. Amplification products were run on a 1% agarose gel and stained using ethidium bromide. Parallel reactions were performed for comparison using HF buffer (Finnzymes product F-518) and GC buffer (Finnzymes product F-519). HF and GC buffers are sold by Finnzymes for use with Phusion DNA polymerase, and the buffer compositions are proprietary. The results are presented in FIG. 1, and show that increasing the concentration of DNA polymerase fusion over the range from 2-6 U per 50 μl reaction increases product yield in the packing buffer, but not in either HF or GC buffer.

EXAMPLE 2

Experiments were performed with different mineral salts using packed DNA polymerase to determine the optimal concentration of salt in the reaction buffers. The reactions were performed as described above in Example 1, with several exceptions. The mineral salts tested were CsCl, KNO3, and CsNO$_3$. The ranges of concentrations of each mineral salt used in the experiments were as follows: CsCl: 50-120 mM; KNO3: 15-110 mM; and CsNO$_3$: 30-100 mM. In addition, each mineral salt was tested in a thermocycling reaction using 20 U of DNA polymerase (Pfu-Sso7d polymerase fusion) were used. The results demonstrate increasing the concentration of mineral salt over the range of 50 to 120 mM per reaction increases product yield in a reaction with 20U DNA polymerase. The results also demonstrate that the optimal concentration range for mineral salts in a packed buffer composition is in the range of 80 and 100 mM.

The invention claimed is:

1. A composition for nucleic acid replication, comprising a mineral salt, ammonium sulfate, and at least one fusion DNA polymerase, said composition having a mineral salt:ammonium sulfate molar ratio in the range from about 30:1 to 240:1, wherein the DNA polymerase(s) concentration is at least 6 units per 50 μl.

2. The composition of claim 1, wherein the mineral salt:ammonium salt molar ratio is in the range from about 30:1 to 80:1.

3. The composition of claim 1, wherein the mineral salt concentration is in the range from 50 mM to 120 mM.

4. The composition of claim 3, wherein the mineral salt concentration is in the range from 80 mM to 100 mM.

5. The composition of claim 1, wherein the ammonium sulfate concentration is in the range from 1 mM to 5 mM.

6. The composition of claim 1, wherein the mineral salt concentration is in the range from 50 mM to 120 mM and the ammonium sulfate concentration is in the range from 1 mM to 5 mM.

7. The composition of claim 1, wherein the composition comprises magnesium sulfate.

8. The composition of claim 7, wherein the magnesium sulfate concentration is in the range from 1 mM to 3 mM.

9. The composition of claim 8, wherein the magnesium sulfate concentration is 2 mM.

10. The composition of claim 1, wherein the composition comprises Tris sulfate buffer.

11. The composition of claim 10, wherein the Tris sulfate concentration is in the range from 15 mM to 50 mM.

12. The composition of claim 11, wherein the Tris sulfate concentration is 30 mM.

13. The composition of claim 10, wherein the pH of the solution is in the range from 8 to 11.

14. The composition of claim 13, wherein the pH is 10.

15. The composition of claim 13, wherein the pH is 9.

16. The composition of claim 1, wherein the mineral salt concentration is in the range from 50 mM to 120 mM, the ammonium sulfate concentration is in the range from 1 mM to 5 mM, and the composition comprises magnesium sulfate at a concentration in the range from 1 mM to 3 mM and Tris sulfate at a concentration in the range from 15 mM to 50 mM.

17. The composition of claim 1, comprising 50 mM mineral salt, 1 mM ammonium sulfate, 30 mM Tris sulfate adjusted to pH 10.0, 2 mM magnesium sulfate, and 0.1% Triton X-100.

18. The composition of claim 1, comprising 80 mM mineral salt, 1.5 mM ammonium sulfate, 30 mM Tris sulfate adjusted to pH 10.0, 2 mM magnesium sulfate, and 0.1% Triton X-100.

19. The composition of claim 1, comprising 100 mM mineral salt, 2 mM ammonium sulfate, 30 mM Tris sulfate adjusted to pH 10.0, 2 mM magnesium sulfate, and 0.1% Triton X-100.

20. The composition of claim 19, wherein essentially all of the anions are sulfate ions.

21. The composition of claim 1, further comprising one or more nucleotides.

22. The composition of claim 1, wherein said DNA polymerase is exo-Pfu-Sso7d or exo-Pfu V93R-Sso7d.

23. The composition of claim 1, wherein the DNA polymerase concentration is in the range of 50 to 100 units per 50 µl.

24. The composition of claim 1, wherein the DNA polymerase concentration is at least 10 units per 50 µl.

25. The composition of claim 1, wherein the DNA polymerase concentration is at least 20 units per 50 µl.

26. The composition of claim 1, wherein the DNA polymerase concentration is in the range of 6 to 25 units per 50 µl.

27. The composition of claim 1, further comprising a nucleic acid template.

28. The composition of claim 1, further comprising a primer.

29. The composition of claim 1, further comprising a polymerization enhancing factor.

30. The composition of claim 1, further comprising one or more nucleotides, one or more nucleic acid polymerases, a nucleic acid template, and a primer.

31. A buffer concentrate for preparing a DNA polymerase reaction solution, wherein dilution by a factor ranging from 2-fold to 20-fold yields the composition of claim 1.

32. The buffer concentrate of claim 31, wherein dilution by a factor ranging from 5-fold to 10-fold yields said composition.

33. A buffer concentrate for preparing a DNA polymerase reaction solution, wherein dilution by 5-fold to 10-fold yields composition of claim 16.

34. A buffer concentrate for preparing a DNA polymerase reaction solution, wherein dilution by 5-fold to 10-fold yields composition of claim 17.

35. A buffer concentrate for preparing a DNA polymerase reaction solution, wherein dilution by 5-fold to 10-fold yields composition of claim 18.

36. The buffer concentrate of claim 31, further comprising one or more nucleotides.

37. The buffer concentrate of claim 31, further comprising one or more nucleic acid polymerases.

38. The buffer concentrate of claim 37, wherein the DNA polymerase is a Pfu-Sso7d or exo-Pfu V93R-Sso7d.

39. The buffer concentrate of claim 37, wherein the DNA polymerase is *Pyrococcus* GB-D-furiosus-Sso7d.

40. The buffer concentrate of claim 31, further comprising a Fen nuclease.

41. The buffer concentrate of claim 31, further comprising a nucleic acid template.

42. The buffer concentrate of claim 31, further comprising a primer.

43. The buffer concentrate of claim 31, further comprising a polymerization enhancing factor.

44. A kit for the replication of a nucleic acid sample, comprising the buffer concentrate of claim 36 and packaging material therefor.

45. The kit of claim 44 further comprising one or more nucleotides, one or more nucleic acid polymerases, a Fen nuclease, one or more primers, a nucleic acid template, or a polymerization enhancing factor.

46. The composition of claim 1, wherein the mineral salt is selected from the group consisting of potassium sulfate, potassium chloride, potassium nitrate, cesium chloride, and cesium nitrate.

47. The composition of claim 46, wherein the mineral salt is potassium sulfate.

48. The composition of claim 1, wherein the mineral salt is a mixture of salts selected from the group consisting of potassium sulfate, potassium chloride, potassium nitrate, cesium chloride, and cesium nitrate.

49. The composition of claim 1, wherein the concentration of the mineral salt component of said composition is in the range of 50 mM and 120 mM.

50. The composition of claim 1; wherein the DNA polymerase is Pfu-Deep Vent-Sso7d.

* * * * *

UNITED STATES PATENT AND TRADEMARK OFFICE
CERTIFICATE OF CORRECTION

| | | |
|---|---|---|
| PATENT NO. | : 7,939,645 B2 | Page 1 of 1 |
| APPLICATION NO. | : 11/651169 | |
| DATED | : May 10, 2011 | |
| INVENTOR(S) | : Michael Borns | |

It is certified that error appears in the above-identified patent and that said Letters Patent is hereby corrected as shown below:

In column 26, line 43, in Claim 50, delete "claim 1;" and insert -- claim 1, --, therefor.

Signed and Sealed this
Fifth Day of July, 2011

David J. Kappos
*Director of the United States Patent and Trademark Office*